US006238913B1

(12) United States Patent
Buckner, III

(10) Patent No.: US 6,238,913 B1
(45) Date of Patent: May 29, 2001

(54) APPARATUS FOR HEATING AND COOLING DEEP WELL PHARMACEUTICAL MICROPLATES

(75) Inventor: Charles Amick Buckner, III, Durham, NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/448,079

(22) Filed: Nov. 23, 1999

(51) Int. Cl.[7] .............................. C12M 1/02; C12M 1/38

(52) U.S. Cl. .................. 435/303.1; 435/809; 435/297.2; 435/288.4; 422/102; 422/104; 165/104.28

(58) Field of Search ......................... 435/6, 287.2, 286.1, 435/286.5, 288.4, 303.1, 305.2, 305.3, 809; 422/99, 102, 104; 165/206, 61, 65, 104.28; 219/439, 400, 428

(56) References Cited

U.S. PATENT DOCUMENTS 4,950,608 * 8/1990 Kishimoto .
5,459,300 * 10/1995 Kasman .
5,601,141 * 2/1997 Gordon et al. .
5,620,894 4/1997 Barger et al. .
5,681,492 * 10/1997 Van Praet .
5,942,432 * 8/1999 Smith et al. .
6,106,784 * 8/2000 Lund et al. .

FOREIGN PATENT DOCUMENTS 8-192058 * 7/1996 (JP) .

* cited by examiner

*Primary Examiner*—William H. Beisner
(74) *Attorney, Agent, or Firm*—Charles E. Dadswell

(57) ABSTRACT

An apparatus for uniformly heating and cooling deep well pharmaceutical microplates when used in fluid connection with a heater/cooler water pump. The apparatus comprises a housing having a divider plate extending transversely through the medial portion of the housing and that defines a matrix of apertures therethrough. A plurality of vertically extending tubes are mounted within a corresponding plurality of the matrix of apertures with the lower end of each tube mounted in a corresponding aperture and the top end extending upwardly from the divider plate and through the open top of the housing. A fluid inlet into the upper chamber of the housing defined by the divider plate, and fluid outlet from the lower chamber of the housing defined by the divider plate is provided in the housing along with a support surface around at least a portion of the perimeter of the upper chamber to support a deep well pharmaceutical microplate in upright position thereon with the plurality of tubes being nestingly received within the interstices defined between the deep wells of the microplate and extending parallel and substantially along the entire length of the deep wells.

31 Claims, 9 Drawing Sheets

APPARATUS FOR HEATING AND COOLING DEEP WELL PHARMACEUTICAL MICROPLATES

TECHNICAL FIELD

The present invention relates to an apparatus for heating and cooling deep well pharmaceutical microplates, and more particularly to an apparatus for heating and cooling deep well microplates that provides for more uniform heating both between wells and within respective wells.

RELATED ART

Pharmaceutical laboratory technicians are familiar with devices that are intended to heat and cool deep well microplates, and the relative inadequacy of known devices to provide for uniform temperature from top to bottom of each deep well as well as uniform temperature among a matrix of deep wells in a pharmaceutical deep well microplate. For example, prior art heating and cooling devices known to applicant tend to concentrate heat at the bottom of the wells of a deep well microplate as well as within the central wells (which are warmer than the outside wells). Also, prior art devices known to applicant for heating and cooling pharmaceutical deep well microplates tend to require an extended period of time to bring the temperature of the wells of the deep well microplate up to a desired temperature. This inherent feature of prior art heating and cooling devices for deep well pharmaceutical microplates is problematic for pharmaceutical laboratory technicians in many laboratory testing situations.

Therefore, applicant's apparatus for heating and cooling deep well pharmaceutical microplates is believed to meet a long-felt need for a heating and cooling apparatus for deep well microplates which overcomes (1) the lack of temperature uniformity and (2) the lack of rapid warm-up of devices presently utilized in the art. The simple-to-use and highly reliable apparatus for heating and cooling deep well pharmaceutical microplates described and claimed hereinbelow meets these and other long-felt needs known to those skilled in the art.

DISCLOSURE OF THE INVENTION

In accordance with the present invention, applicant provides an apparatus for modulating the temperature of a microplate of the type having an open bottom with interstices defined therewithin between the wells of the microplate. The apparatus is adapted for being fluidly connected with a conventional heater/cooler water pump such as the LAUDA BRINKMANN Model RC20. The apparatus comprises a housing with a bottom, sides, and an open top. A divider plate extends transversely through a medial portion of the housing between the top and bottom thereof so as to create a bottom closed chamber therebeneath and an upper chamber thereabove. A plurality of vertically upwardly extending tubes are provided wherein the bottom end of each of the tubes is mounted within the divider plate and the top end of each of the tubes extends upwardly from the divider plate and through the open top of the housing. A support surface is provided around a portion of the perimeter of the upper chamber for supporting a pharmaceutical microplate in upright position thereon wherein the plurality of upwardly extending tubes are oriented so as to be nestingly received within the interstices defined between the wells of the microplate. In this manner heated or cooled fluid introduced from a heater/cooler water pump and into the upper chamber of the housing will rise up around the wells of a pharmaceutical microplate positioned in the upper chamber of the apparatus until the fluid reaches the level of the tubes. The fluid will then flow downwardly through the tubes into the bottom chamber of the housing and out therefrom to the heater/cooler water pump.

It is therefore an object of the present invention to provide an apparatus for heating and cooling deep well pharmaceutical microplates for use in combination with a heater/cooler water pump to provide uniform temperature from top to bottom of each deep well as well as among the entire matrix of deep wells of the microplate.

It is another object of the present invention to provide an apparatus for heating and cooling deep well pharmaceutical microplates for use in fluid connection with a heater/cooler water pump which provides for relatively rapid heating of the deep wells to a desired temperature due to inherently rapid heat transfer performance of the apparatus.

Some of the objects of the invention having been stated hereinabove, other objects will become evident as the description proceeds, when taken in connection with the accompanying drawings as best described hereinbelow.

BEST MODE FOR CARRYING OUT THE INVENTION

Figure 1:
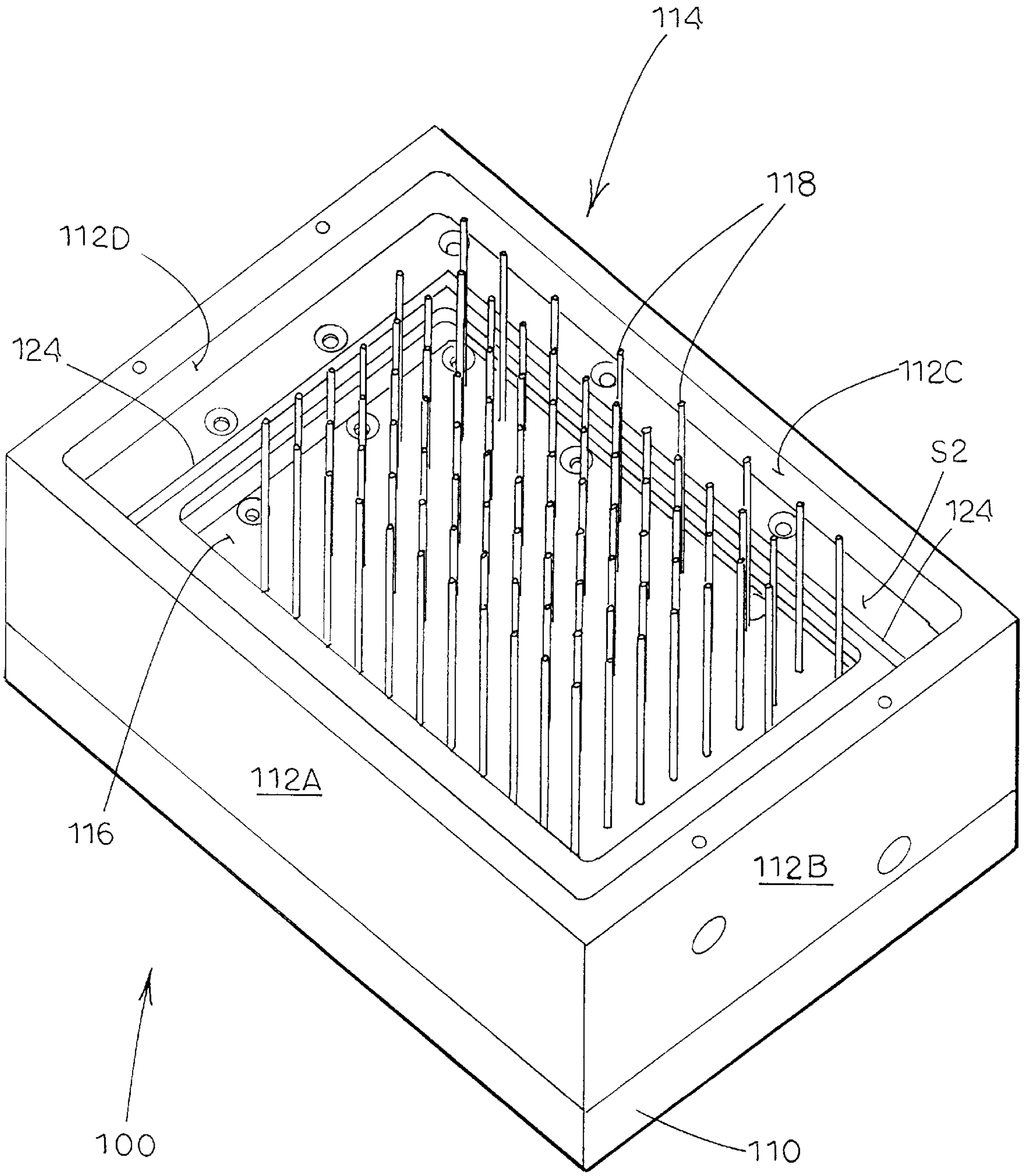
FIG. 1 is a perspective view of the apparatus for heating and cooling deep well pharmaceutical microplates according to the present invention.
Figure 2:
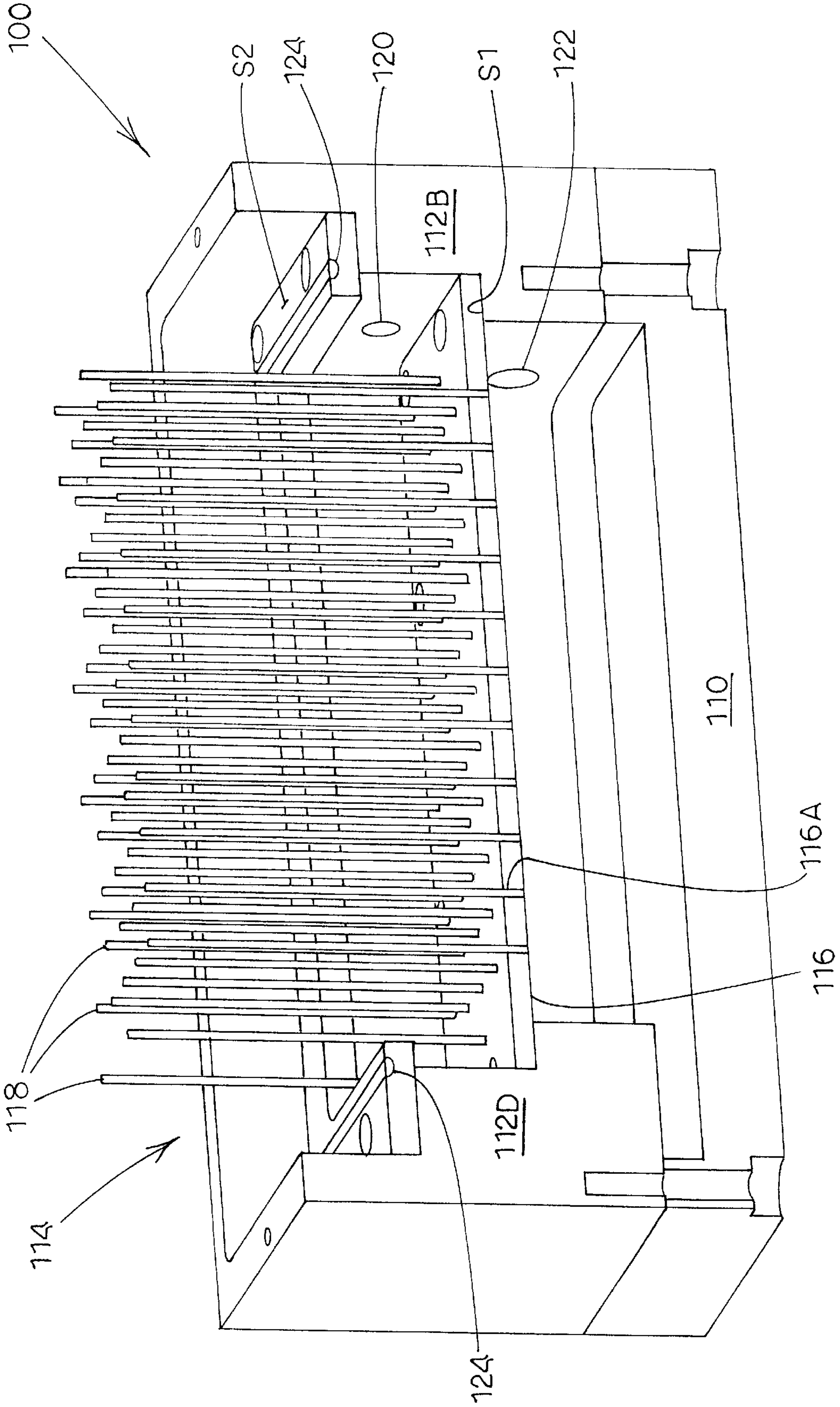
FIG. 2 is a vertical cross-sectional view of the heating and cooling apparatus shown in FIG. 1.
Figure 3:
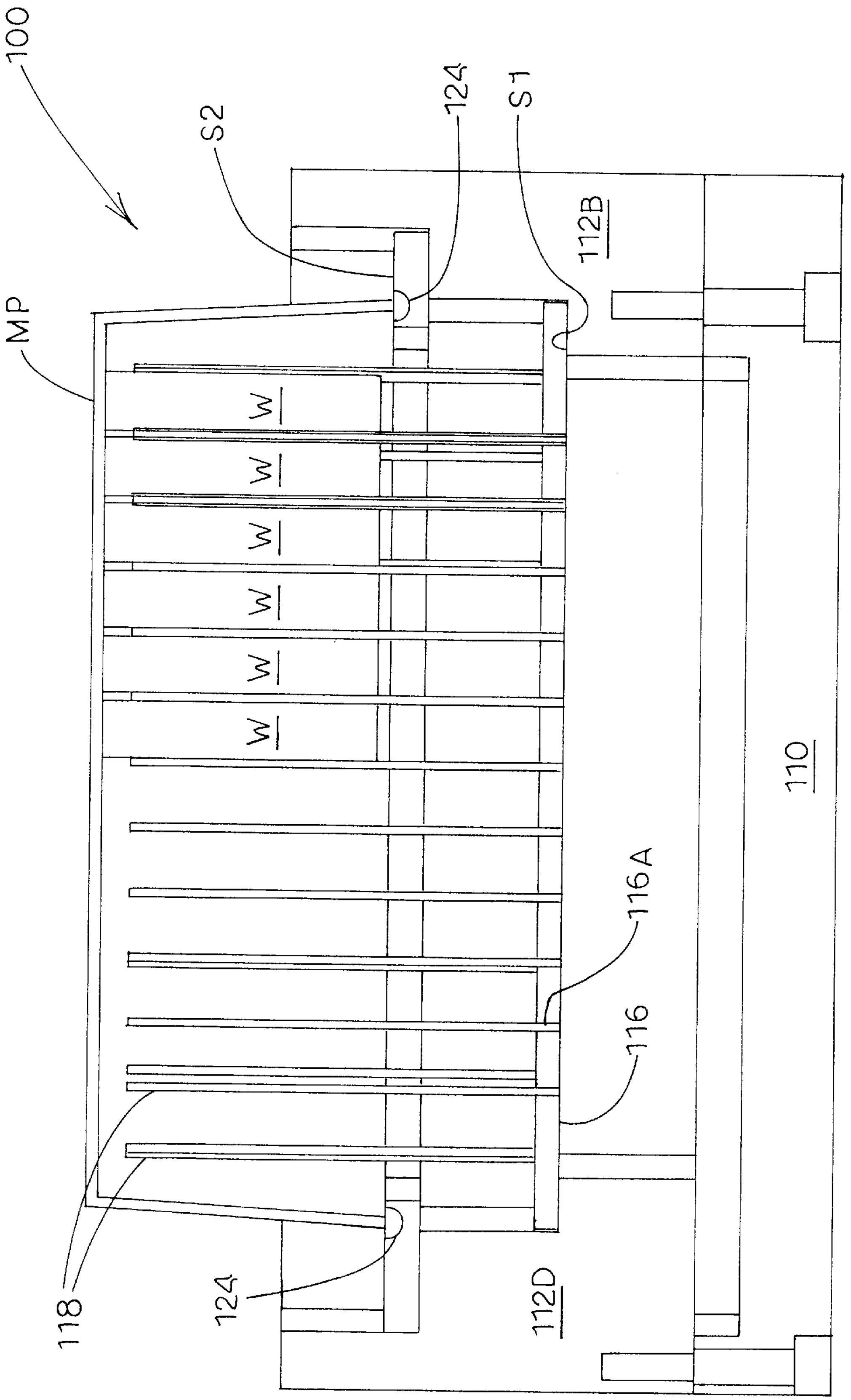
FIG. 3 is a vertical cross-sectional view of the heating and cooling apparatus shown in FIG. 1 with a deep well pharmaceutical microplate positioned in an upright position thereon.
Figure 4:
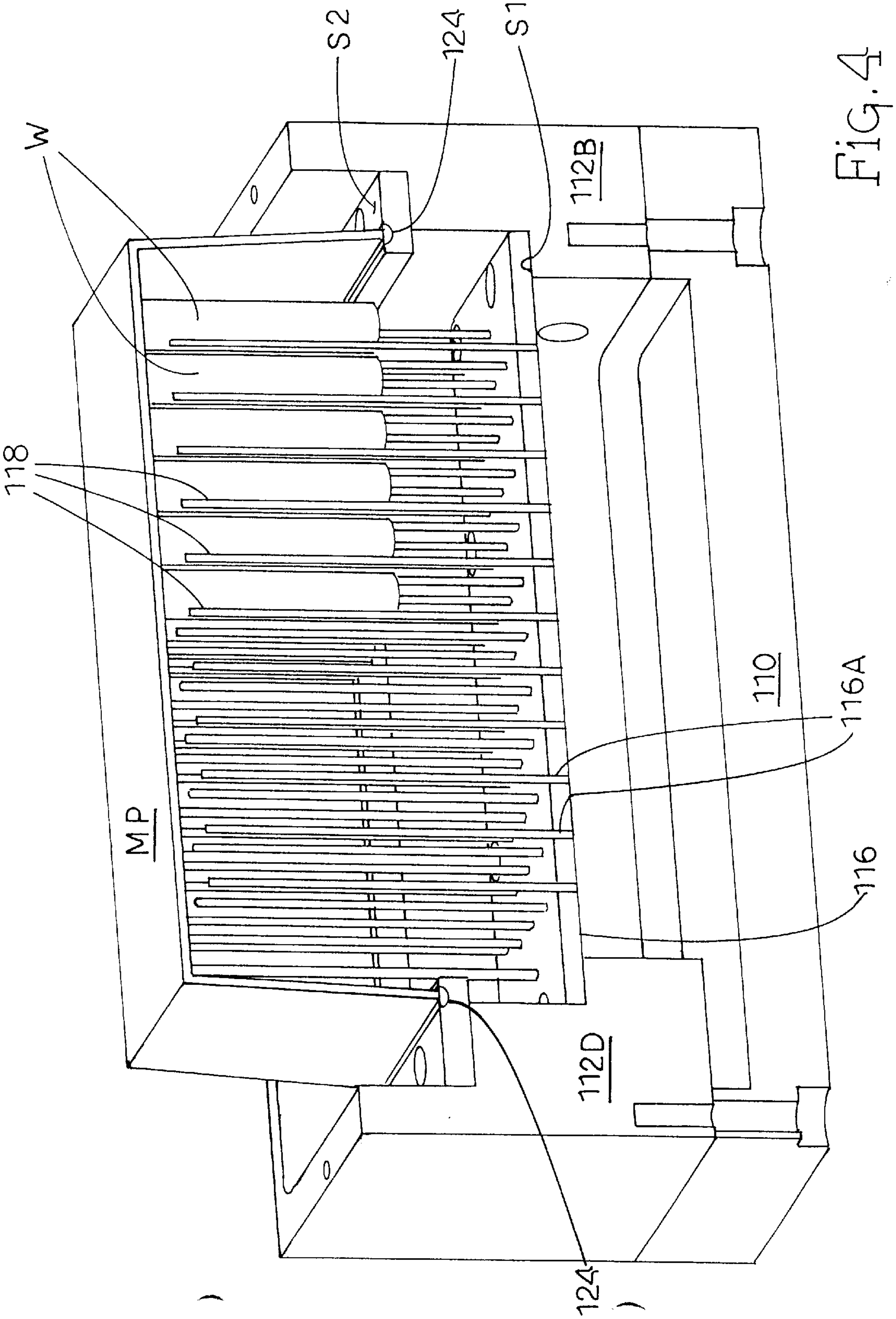
FIG. 4 is a vertical cross-sectional view of the heating and cooling apparatus similar to FIG. 3 with a deep well pharmaceutical microplate positioned in upright position thereon.
Figure 5:
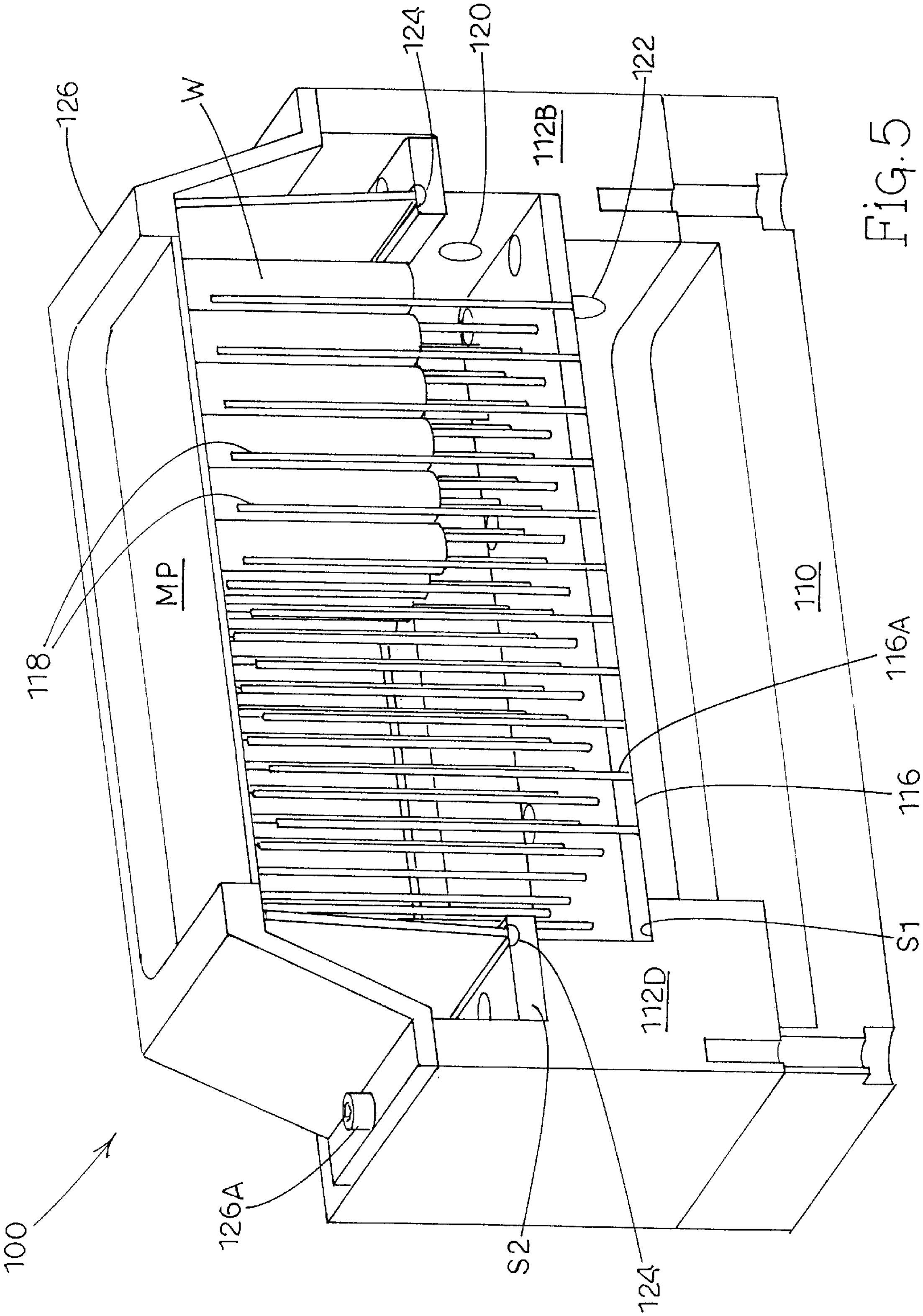
FIG. 5 is a vertical cross-sectional view similar to FIGS. 3 and 4 but also depicting a removable clamp for securely holding a deep well pharmaceutical microplate in position on the apparatus.
Figure 6:
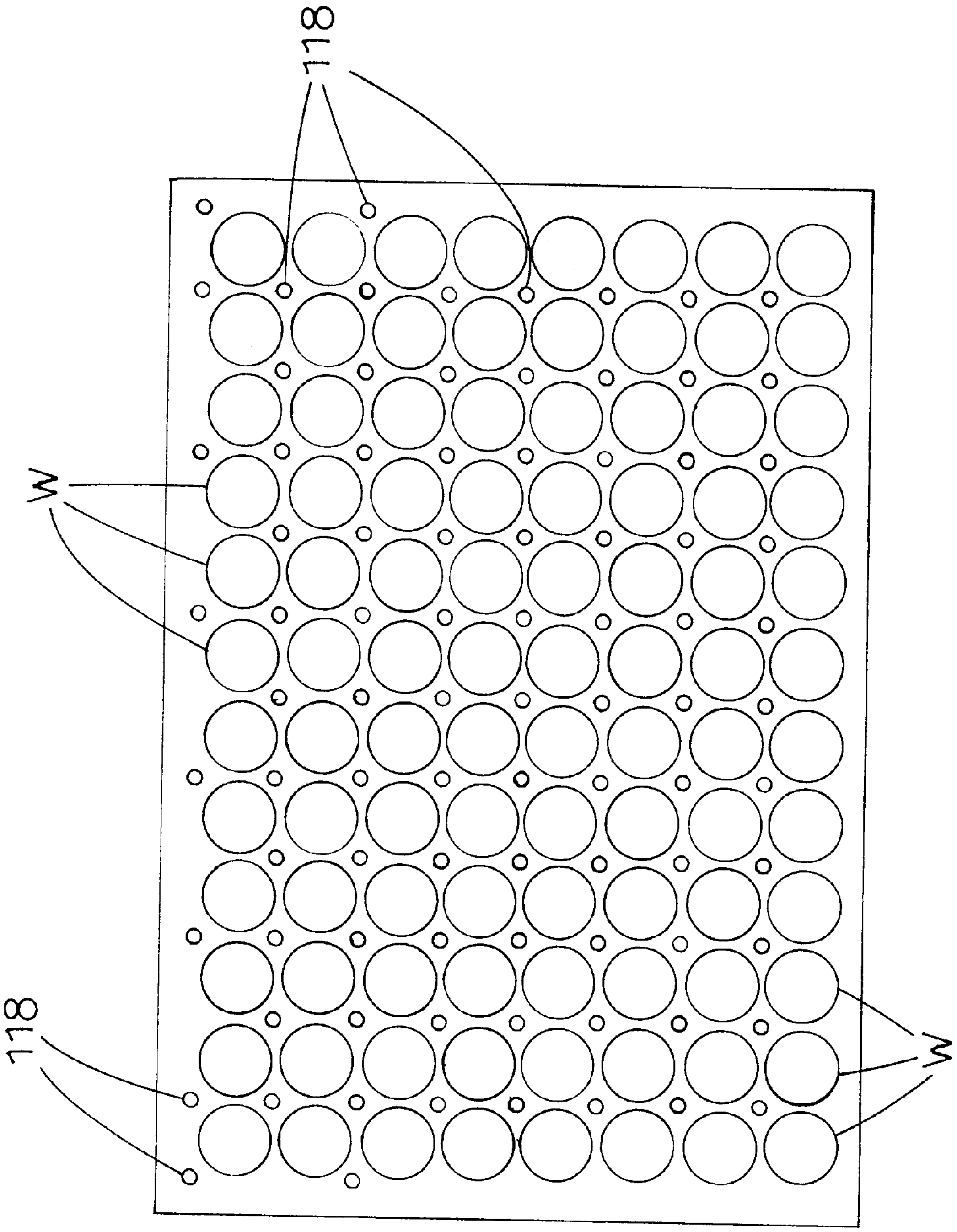
FIG. 6 is a schematic diagram showing a top view of a pharmaceutical deep well microplate and the deep wells thereof and the positions of the fluid tubes of the apparatus of the present invention therebetween.

Applicant has developed an apparatus for heating and cooling deep well pharmaceutical microplates (e.g., a 96 well microplate) that provides uniform temperature from top to bottom of each deep well as well as from well to well among the matrix of deep wells in a deep well microplate. The apparatus can be fluidly connected in a closed loop to conventional heater/cooler water pumps such as the LAUDA BRINKMANN Model RC20 available from Brinkmann Instruments, Inc.; the TECAN Model No. Genesis RSP 150 available from Tecan U.S.A., Inc.; the PACKARD Model No. Multiprobe II available from Packard, Inc.; and the GILSON Model No. 215 and 233 available from Gilson, Inc. The capability of applicant's apparatus for heating and cooling deep well pharmaceutical microplates to rapidly achieve a uniform temperature both from well-to-well as well as from top-to-bottom of respective wells of a deep well microplate is particularly desirable for use in pharmaceutical testing laboratories for many types of testing including in vitro liver fraction incubations, bioanalytical sample preparation, receptor binding assays, tissue culture assays, and DNA sequencing.

Further, although applicant will describe the apparatus of the invention in terms of heating and cooling a 96 well deep well microplate, it will be appreciated that the apparatus can be used for heating and cooling a wide variety of deep well microplates as well as a variety of non-deep well microplates, and applicant does not intend to limit the invention in any manner whatsoever by the representative description of heating and cooling of a 96 well deep well microplate as described herein. Quite to the contrary, applicant intends for the invention to encompass an apparatus for heating and cooling any size and type of deep well microplate and non-deep well microplate, and for the description set forth below to be used for the purpose of illustration only and not for the purpose of limitation of the invention which is intended to be defined by the claims appended hereto.

Referring now to FIGS. 1–6 of the drawings, a preferred embodiment of the apparatus for heating and cooling deep well pharmaceutical microplates in accordance with the present invention is shown and generally designated 100. Apparatus 100 is intended for use in combination with a conventional heater/cooler water pump (not shown) and comprises a housing consisting of a bottom 110 and four sides 112A–112D that define an open top generally designated 114. A divider plate 116 extends transversely through the housing between the top and bottom thereof and rests on a shoulder S1 provided on the inside surface of each of sides 112A–112D. Divider plate 116 includes a matrix of rows and columns of apertures 116A therethrough. As shown in the drawings, divider plate 116 is provided with a total of 87 apertures 116A in a matrix of rows and columns. Specifically, apertures 116A are arranged in a matrix of seven rows of eleven apertures and eleven columns of seven apertures with an "envelope" often apertures around the top of the matrix (see FIG. 6) to facilitate engagement of a 96 well microplate as will be described hereinafter.

It should be appreciated that applicant's invention is intended to encompass many other matrix configurations comprising many different numbers of apertures 116A therethrough in order to best heat and cool different size deep well pharmaceutical micro plates that may be positioned thereon. Applicant's particular matrix configuration of apertures 116A is believed to be particularly well suited for a deep well pharmaceutical microplate of 96 wells, but applicant's invention as noted hereinbefore is not in any way intended to be limited only to the matrix configuration of apertures 116A described herein.

Apparatus 100 further includes a plurality of upwardly extending tubes 118 corresponding to the number of apertures 116A individer plate 116. The bottom end of each tube 118 is mounted within a corresponding one of apertures 116A of divider plate 116 and the top end of each tube 118 extends upwardly from the divider plate and through open top 114 of the housing of apparatus 100. Referring particularly to FIGS. 3–6, it will be appreciated that each well W of microplate MP will have at least one tube 118 adjacent thereto and, in practice, the substantial majority of wells W of deep well microplate MP will have two or more of tubes 118 adjacent thereto as can be particularly appreciated with reference to the schematic diagram shown in FIG. 6. The advantages of having at least one tube 118 adjacent each well W of deep well microplate MP will be explained in more detail hereinafter. Apparatus 100 further includes a fluid inlet 120 into the upper chamber defined by divider plate 116 and a fluid outlet 122 from the lower chamber defined by divider plate 116.

A support surface consisting of a shoulder S2 is provided around the perimeter of the upper chamber above divider plate 116 for supporting deep well pharmaceutical microplate MP in an upright position thereon so that tubes 118 will be nestingly received within interstices defined between wells W of microplate MP and that tubes 118 will extend parallel to and substantially along the entire length of deep wells W. The bottom edge of each of the four sides deep well microplate MP will be received by a resilient seal 124 that is mounted in support shoulder S2 extending around the perimeter of the upper chamber of apparatus 100. Finally, an optional clamp 126 (see FIG. 5) can be used to secure deep well microplate MP to apparatus 100 as needed. Clamp 126 is secured to the top of housing sides 112A–112D by suitable means such as a screw and bolt assembly 126A (see FIG. 5). Applicant contemplates that clamp 126A will not be necessary for certain uses of apparatus 100 in heating and cooling deep well microplate MP but that it may be used in other applications as a matter of choice. Moreover, applicant contemplates that clamp mechanisms other than clamp 126 can be used to secure deep well microplate MP to apparatus 100 and all are intended to fall within the scope of the present invention.

Applicant contemplates that apparatus 100 including bottom 110, sides 112A–112D, divider plate 116, and tubes 118 can be made from materials such as DELRIN™. Resilient seal 124 is preferably formed from an elastomeric material such as rubber, although seal 124 can be formed from other similar materials. Also, although applicant has referred hereinabove to deep well microplates MP, it should be stated that the present invention is also intended to encompass an apparatus that will accommodate conventional, non-deep well microplates.

Operation of Heating and Cooling Apparatus for Deep Well Microplates

In use, a fluid such as water is pumped from a heater/coolerwater pump (not shown) to fluid inlet 120 of apparatus 100. The water flows onto divider plate 116 which prevents it from flowing to the bottom chamber of apparatus 100. Thus, the water flows upwardly into the upper chamber of apparatus 100 above divider plate 116 until it reaches the top of tubes 118. The water then flows down through the tubes into the bottom chamber of apparatus 100 beneath divider plate 116. In this manner, continuous water flow is provided around and along substantially the entire length of deep wells W of microplate MP as the water enters through fluid inlet 120 and exits through fluid outlet 122. The continuous water flow along the substantially the entire depth of deep wells W as well as between the entire matrix of deep wells W serves to rapidly bring the temperature of the contents of wells W to a desired temperature and to maintain a substantially uniform temperature along the entire length of each well and between all of the matrix of deep wells W defined within deep well microplate MP.

As would be known to those skilled in the art, a heater/cooler water pump (not shown) can be used to pump either a warm fluid or a cool fluid to apparatus 100 as a matter of user choice. If a warm fluid such as water (e.g., preferably a solution of 80% water and 20% alcohol) is pumped to apparatus 100, applicant has discovered that at a desired temperature such as 37° Centigrade the uniformity will vary only about ±0.10° Centigrade along the length of well W and about 0.10° Centigrade between the matrix of wells W. Further, applicant has discovered that apparatus 100 can heat the contents of deep well microplate MP from room temperature to 37° Centigrade within about 1 minute due to its ability to rapidly achieve a desired uniform temperature within wells W of deep well microplate MP. Cooling with a cool fluid such as water to a desired temperature of 4° Centigrade with apparatus 100 will also only allow a variance of about 0.10° Centigrade along the length of wells W and between the matrix of wells W. Further, although applicant has described the use of apparatus 100 with a solution of water and alcohol, applicant believes that a gas such as nitrogen could also be utilized effectively to uniformly heat and cool wells W of deep well microplate MP.

Although many uses of apparatus 100 are contemplated by applicant, typical pharmaceutical samples that would be heated or cooled by apparatus 100 include the following: liver microsones, S9 fraction, serum, urine, new chemical entity (NCE) solutions, and cellular fractions. Further, applicant has provided a slot in the back of the housing of apparatus 100 so that fluid will flow from the upper chamber to the lower chamber and the apparatus not overflow if microplate MP is removed from the apparatus during operation thereof.

Alternative Embodiment of the Invention

Figure 7:
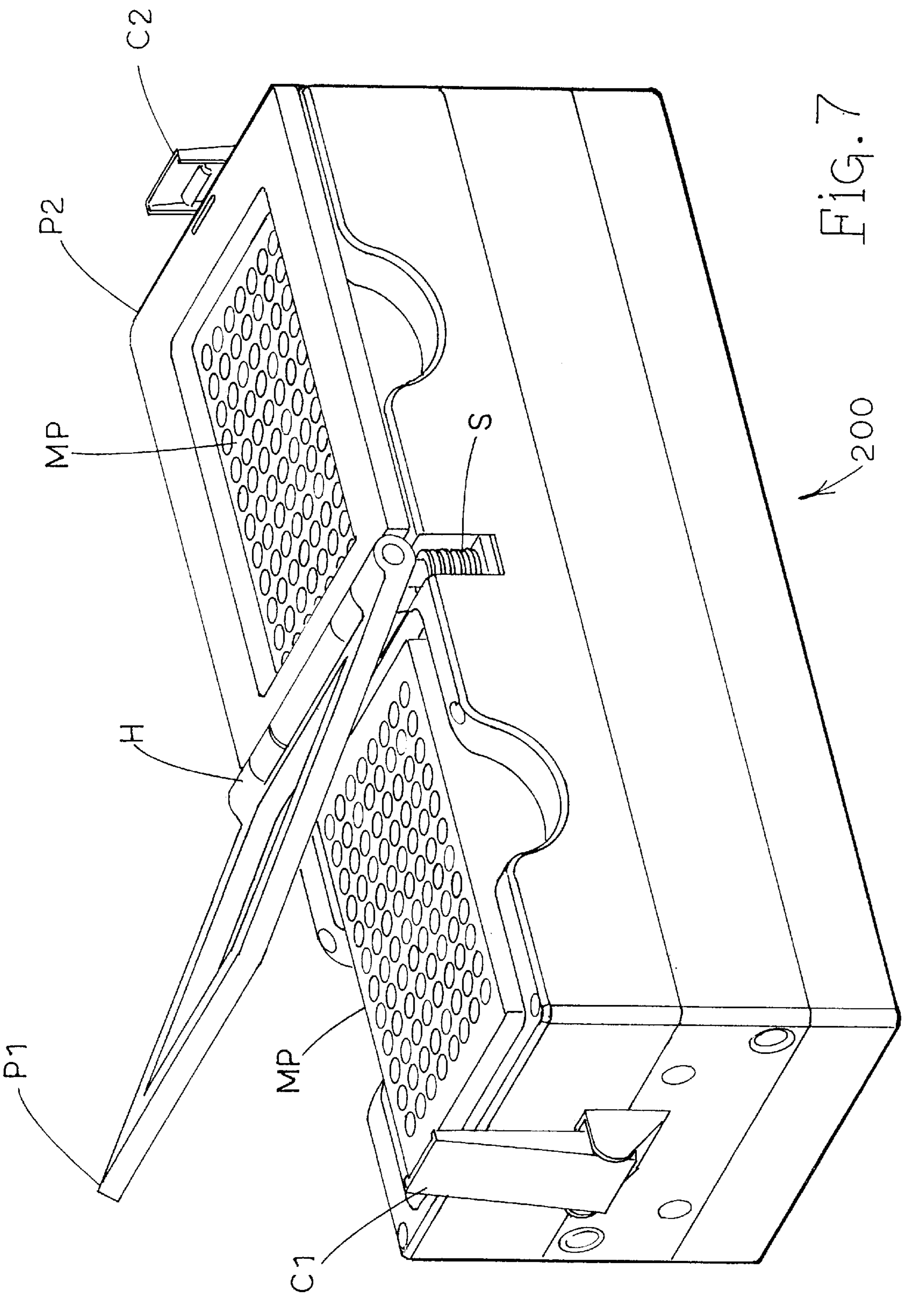
FIG. 7 is a perspective view of a second embodiment of the apparatus for heating and cooling deep well pharmaceutical microplates according to the present invention which provides for simultaneous heating and/or cooling of two microplates.
Figure 8:
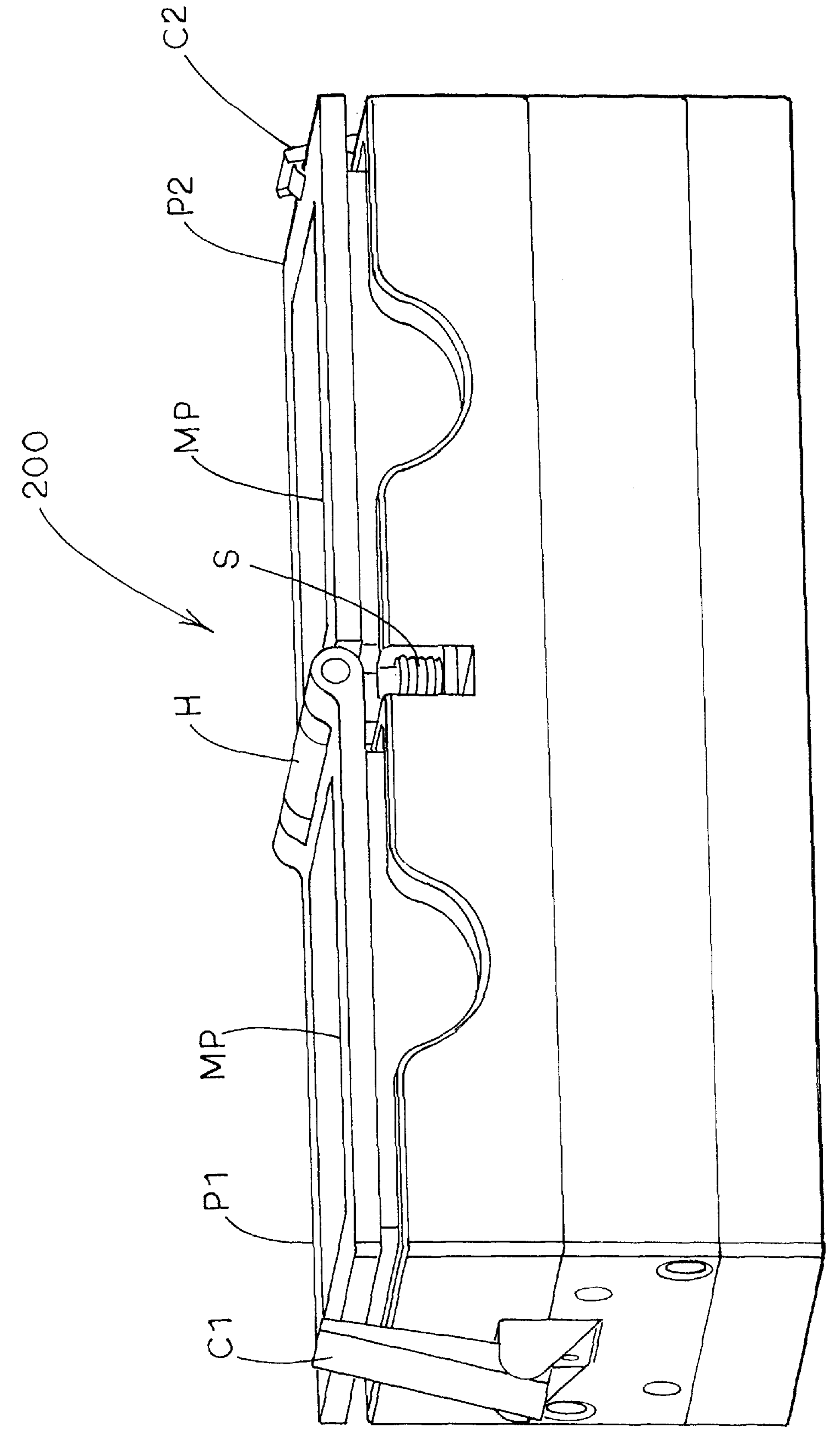
FIG. 8 is a perspective view of the apparatus of FIG. 7 with the two hold down panels in a raised position and clamped over two microplates having a plurality of sealing gaskets resting thereon.
Figure 9:
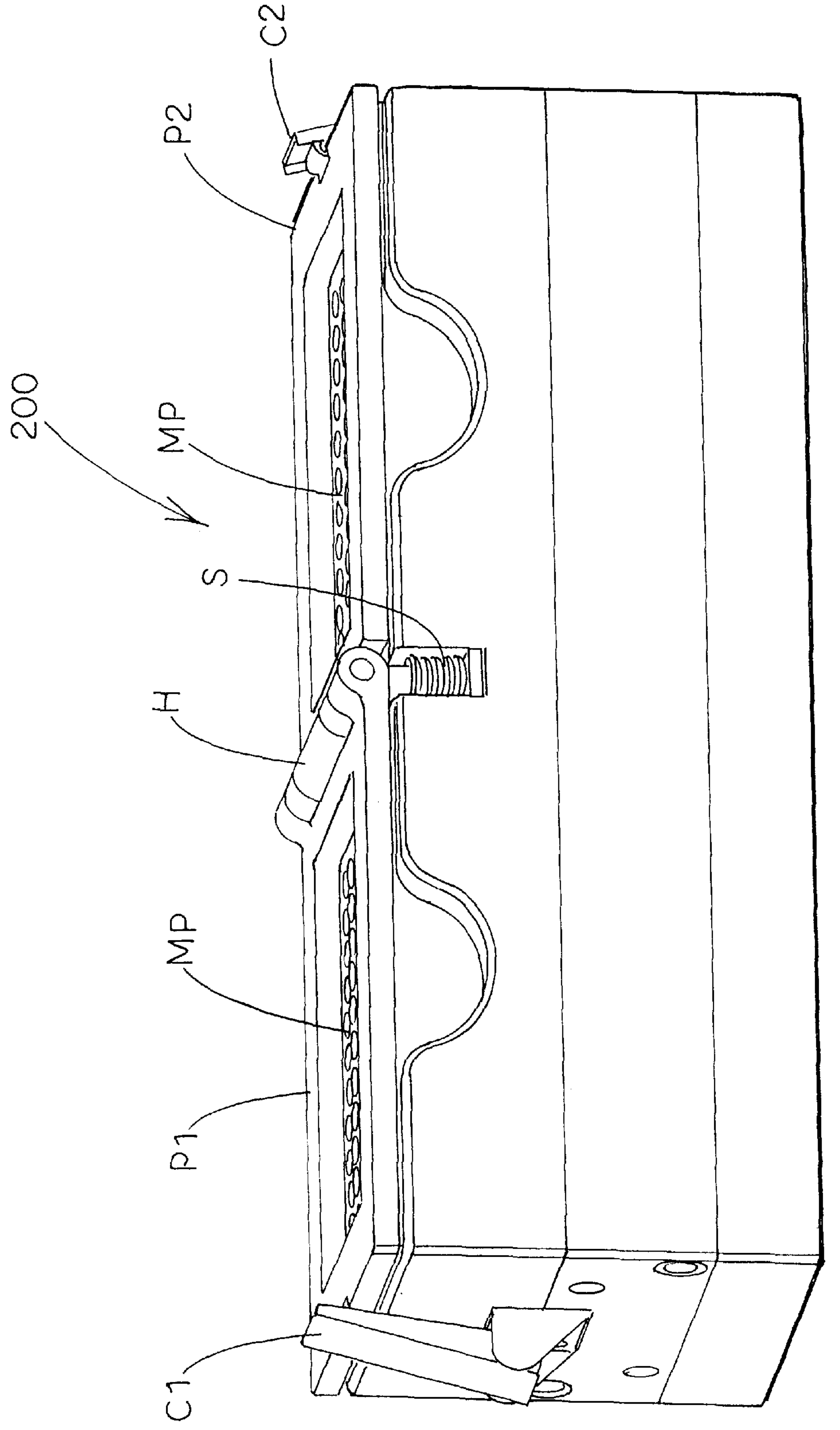
FIG. 9 is a perspective view of the apparatus of FIG. 7 with the two hold down panels in a lowered position and clamped over two microplates, having a smaller number of sealing gaskets resting thereon than in FIG. 8.

Referring now to FIGS. 7–9 of the drawings, applicant will describe a second embodiment of the apparatus of the invention, generally designated 200, for heating and cooling deep well pharmaceutical microplates as well as non-deep well pharmaceutical microplates to provide a uniform temperature from top to bottom of each well as well as from well-to-well among the matrix of wells in a microplate. Apparatus 200 is similar in structure and function to apparatus 100 except apparatus 200 can accommodate two microplates MP for simultaneous heating, cooling or heating and cooling. Applicant contemplates that apparatus 200 will provide for each heating and cooling unit for a respective microplate MP to have its own water flow as described hereinbefore and depicted in FIGS. 1–6 of the drawings. Although applicant contemplates that apparatus 200 can be formed in a multiplicity of different ways, FIGS. 7–9 illustrate apparatus 200 being provided with hinge H about which each of two hold down panels P1, P2 pivot in order to be closed upon their respective microplate MP. Also, corresponding clamps C1, C2, respectively, are provided for engaging the outside edge of hold down panels P1, P2 when they are closed upon the respective microplate beneath each of hold down panels P1, P2.

Although hinge H could be formed in a multiplicity of ways, applicant contemplates that hinge H will be urged downwardly by a plurality of resilient disk springs S along the longitudinal axis thereof in order to resiliently bias hinge H downwardly. In this fashion, as hold down panels P1, P2 are lowered and clamped at their outside edges to clamps C1, C2, respectively, disk springs S of hinge H are compressed so as to allow the hinge to rise or be compressed so as to allow panels P1, P2 to engage microplates MP when they are elevated by sealing gaskets (not shown) resting thereon (see FIG. 8). If fewer sealing gaskets are placed upon microplates MP, hold down panels P1, P2 will be urged downwardly by springs S when panels P1, P2 are engaged by corresponding clamps C1, C2 (see FIG. 9).

The application of which this description and claims form a part may be used as a basis for priority in respect of any subsequent application. The claims of such subsequent application may be directed to any feature or combination of features described herein. They may take the form of product, composition, process or use claims and may include, by way of example and without limitation, one or more of the following claims.

It will be understood that various details of the invention may be changed without departing from the scope of the invention. Furthermore, the foregoing description is for the purpose of illustration only, and not for the purpose of limitation—the invention being defined by the claims.

What is claimed is:

1. An apparatus for modulating the temperature of a pharmaceutical microplate comprising:

(a) a housing having a bottom, sides, and an open top;

(b) a divider plate extending transversely through a medial portion of said housing between the top and bottom thereof so as to create a bottom closed chamber therebeneath and an upper open chamber thereabove;

(c) a plurality of vertically upwardly extending tubes wherein the bottom end of each of said tubes is mounted within said divider plate and the top end of each of said tubes extends upwardly from said divider plate and through said open top of said housing; and (d) a support surface provided around a portion of the perimeter of said upper chamber for supporting a pharmaceutical microplate in upright position thereon wherein said plurality of upwardly extending tubes are oriented so as to be nestingly received within the interstices defined between the wells of said microplate;

whereby heated or cooled fluid introduced from a heater/cooler water pump and into said upper chamber of said housing will rise up and around the wells of a pharmaceutical microplate positioned in the upper chamber of said apparatus.

2. The apparatus of claim 1, wherein said housing comprises four sides and is rectangular.

3. The apparatus of claim 1, wherein said divider plate includes a matrix of apertures therein.

4. The apparatus of claim 3, wherein said matrix of said divider plate comprises a plurality of rows and columns of apertures.

5. The apparatus of claim 4, wherein said divider plate comprises 87 apertures.

6. The apparatus of claim 3, wherein the bottom end of each of said tubes is mounted within a corresponding one of said matrix of apertures.

7. The apparatus of claim 1, wherein said plurality of tubes extends upwardly beyond said sides of said housing.

8. The apparatus of claim 1, wherein said plurality of tubes comprises 87 tubes.

9. The apparatus of claim 1, wherein said support surface comprises a shoulder around the inside perimeter of said upper chamber and includes a resilient seal therearound for sealingly receiving the bottom perimeter edge of a pharmaceutical microplate positioned in an upright position on said shoulder.

10. The apparatus of claim 9, wherein said plurality of tubes extend parallel to and along substantially the entire length of said wells when said microplate is positioned on said support surface of said apparatus.

11. The apparatus of claim 9, wherein 2 or more of said tubes are positioned adjacent at least the substantial majority of the wells of a pharmaceutical microplate.

12. The apparatus of claim 9, comprising a removable clamp to sealingly secure a pharmaceutical microplate to said shoulder of said upper chamber.

13. The apparatus of claim 1, wherein a 96 hole pharmaceutical microplate is mounted on said heating and cooling apparatus.

14. The apparatus of claim 1, including a fluid inlet into said upper chamber of said housing and a fluid outlet from said lower chamber of said housing.

15. The apparatus of claim 14, wherein said heated or cooled fluid is introduced into said upper chamber through said fluid inlet and will rise up and around the wells of said pharmaceutical microplate until the fluid reaches the level of said tubes, and then flow downwardly through said tubes into said bottom chamber of said housing and out therefrom through said fluid outlet.

16. The apparatus of claim 14, wherein said apparatus is in fluid connection to a heater/cooler water pump.

17. The apparatus of claim 16, wherein said apparatus will maintain the well-to-well temperature within a pharmaceutical microplate at 37° C.±0.10° C. when heating and 4° C.±0.10° C. when cooling.

18. The apparatus of claim 16, wherein said heater/cooler water pump circulates a fluid solution of water and alcohol through said heating and cooling apparatus to heat or cool a pharmaceutical microplate.

19. The apparatus of claim 1, wherein said apparatus comprises two housings and is adapted to receive and heat and/or cool two pharmaceutical microplates simultaneously.

20. An apparatus for heating and cooling a pharmaceutical microplate of the type having an open bottom with interstices defined therewithin between the wells of said microplate, said apparatus being adapted to be used in fluid connection with a heater/cooler water pump and comprising:

(a) a housing having a bottom, four sides, and an open top;

(b) a divider plate extending transversely through a medial portion of said housing and between the top and bottom thereof so as to create a bottom closed chamber therebeneath and an upper open chamber thereabove, said divider plate including a matrix of rows and columns of apertures therethrough;

(c) a plurality of vertically upwardly extending tubes wherein the bottom end of each of said tubes is mounted within a corresponding one of said matrix of apertures and the top end of each of said tubes extends upwardly from said divider plate and through said open top of said housing;

(d) a fluid inlet into said upper chamber of said housing and a fluid outlet from said lower chamber of said housing; and (e) a support surface and seal provided around the perimeter of said upper chamber for sealingly supporting a pharmaceutical microplate in upright position thereon wherein said plurality of upwardly extending tubes are oriented so as to be nestingly received within the interstices defined between the wells of said microplate and to extend parallel to and substantially along the entire length of said wells;

whereby heated or cooled fluid introduced from a heater/cooler water pump and into said upper chamber of said housing will rise up and around the wells of a pharmaceutical microplate positioned in the upper chamber of said apparatus until the fluid reaches the level of said tubes, and then flow downwardly through said tubes into said bottom chamber of said housing and out therefrom to the heater/cooler water pump.

21. The apparatus of claim 20, wherein said divider plate comprises 87 apertures.

22. The apparatus of claim 20, wherein said plurality of tubes extends upwardly beyond said sides of said housing.

23. The apparatus of claim 20, wherein said plurality of tubes comprises 87 tubes.

24. The apparatus of claim 20, wherein said support surface comprises a shoulder around the inside perimeter of said upper chamber and said seal comprises a resilient seal therearound for sealingly receiving the bottom perimeter edge of a pharmaceutical microplate positioned in an upright position on said shoulder.

25. The apparatus of claim 24, wherein 2 or more of said tubes are positioned adjacent at least the substantial majority of the wells of a pharmaceutical microplate.

26. The apparatus of claim 24, comprising a removable clamp to sealingly secure a pharmaceutical microplate to said shoulder of said upper chamber.

27. The apparatus of claim 20, wherein a 96 hole pharmaceutical microplate is mounted on said heating and cooling apparatus.

28. The apparatus of claim 20, wherein said heating and cooling apparatus is in fluid connection to a heater/cooler water pump.

29. The apparatus of claim 20, wherein said apparatus will maintain the well-to-well temperature within a pharmaceutical microplate at 37° C.±0.10° C. when heating and 4° C.±0.10° C. when cooling.

30. The apparatus of claim 20, wherein said heater/cooler water pump circulates a fluid solution of water and alcohol through said heating and cooling apparatus to heat or cool a pharmaceutical microplate.

31. The apparatus of claim 20, wherein said apparatus comprises two housings and is adapted to receive and heat and/or cool two pharmaceutical microplates simultaneously.

* * * * *